(12) United States Patent
Repollés Moliner et al.

(10) Patent No.: US 8,106,224 B2
(45) Date of Patent: Jan. 31, 2012

(54) STEREOSPECIFIC METHOD FOR THE PREPARATION OF DIOXA-BICYCLOOCTANE NITRATE COMPOUNDS

(75) Inventors: José Repollés Moliner, Barcelona (ES);
Francisco Pubill Coy, Barcelona (ES);
Lydia Cabeza Llorente, Barcelona (ES); Joan Martínez Bonnin, Barcelona (ES)

(73) Assignee: Lacer, S.A., Barcelona (ES)

( * ) Notice: Subject to any disclaimer, the term of this patent is extended or adjusted under 35 U.S.C. 154(b) by 490 days.

(21) Appl. No.: 12/389,929

(22) Filed: Feb. 20, 2009

(65) Prior Publication Data
US 2010/0160652 A1    Jun. 24, 2010

(30) Foreign Application Priority Data
Dec. 19, 2008    (EP) ..................... 08382079

(51) Int. Cl.
*C07D 493/04* (2006.01)
(52) U.S. Cl. .................................... 549/464
(58) Field of Classification Search ............ 549/464
See application file for complete search history.

(56) References Cited

U.S. PATENT DOCUMENTS

| | | | |
|---|---|---|---|
| 4,364,953 A | 12/1982 | Klessing et al. | |
| 2001/0051735 A1 | 12/2001 | Moliner et al. | |
| 2006/0235052 A1 | 10/2006 | Moliner et al. | |
| 2009/0220662 A1 * | 9/2009 | Tachdjian et al. | 426/536 |

FOREIGN PATENT DOCUMENTS

| | | |
|---|---|---|
| EP | 1 120 419 A1 | 8/2001 |
| WO | WO 00/20420 | 4/2000 |
| WO | WO-00/20420 A1 | 4/2000 |
| WO | WO 2005/037842 | 4/2005 |
| WO | WO-2005/037842 A1 | 4/2005 |

OTHER PUBLICATIONS

XP002520794, Database WPI Week 19905, Thomson Scientific, London, GB, AN 1991-031987, (1991).

* cited by examiner

*Primary Examiner* — Bernard Dentz
(74) *Attorney, Agent, or Firm* — Blank Rome LLP

(57) ABSTRACT

This invention relates to a new method for the stereospecific thiocarboxylation and nitration of organic compounds for the preparation of compounds according to formula (I):

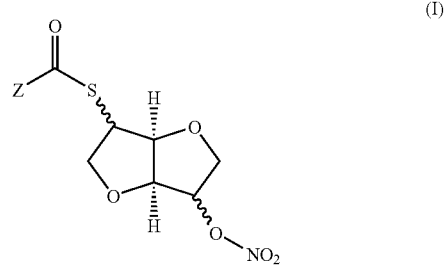

comprising the following steps:
(a) reacting a compound of formula (II):

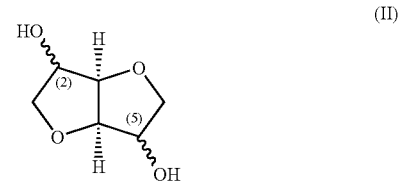

with a sulfonic derivative of formula (III)

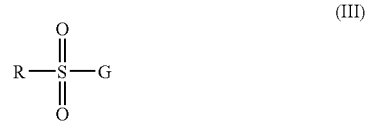

wherein the R is chosen from the groups $C_{1-3}$-alkyl, $C_{1-3}$-alkyl substituted with 1 to 3 halogen atoms, phenyl, $C_{1-3}$-alkyl-phenyl and $C_{1-3}$-alkyl-phenyl wherein the alkyl is substituted with 1 to 3 halogen atoms and G is a halogen atomo or a group —O—$SO_2$—R wherein R is as hereinabove defined to yield a compound of formula (IV)
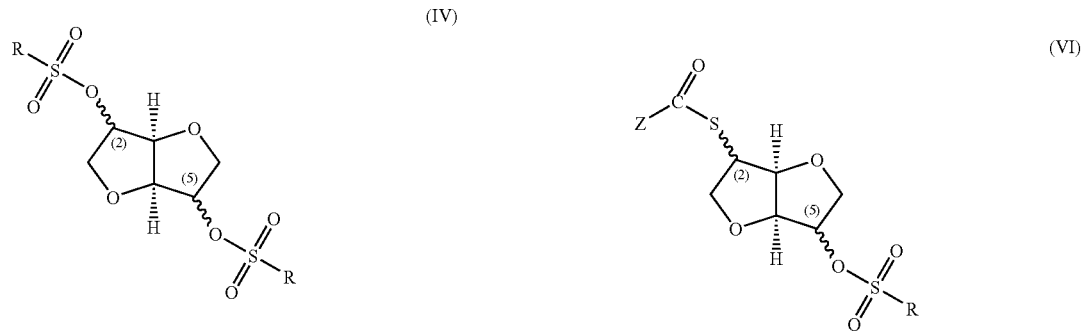
(b) treating compound (IV) with a thiocarboxylic acid of formula (V) or a salt thereof:
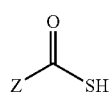
wherein Z is as defined above, to yield compound (VI)
and
(c) treating compound (VI) with tetrabutylammonium nitrate to yield a compound of formula (I).
18 Claims, No Drawings

STEREOSPECIFIC METHOD FOR THE PREPARATION OF DIOXA-BICYCLOOCTANE NITRATE COMPOUNDS

CROSS-REFERENCE TO RELATED APPLICATIONS

The present application claims the benefit of European Application No. 08382079.5 filed Dec. 19, 2008, the entire disclosure of which is incorporated by reference herein.

FIELD OF THE INVENTION

The present invention relates to a new stereospecific method for the preparation of dioxa-bicyclooctane nitrate compounds.

BACKGROUND ART

The nitric acid esters of organic compounds, commonly known as nitrated organic compounds, are known and have been used as vasodilating agents for some time. Among these, the usefulness of mono- and di-nitrated isosorbide is well known, and furthermore, compounds with vascular and coronary activities based on substitution reactions of the free hydroxyl group of isosorbide mononitrate have been described.

Patent application WO 00/20420 describes isosorbide mononitrates wherein the free hydroxyl group is esterified with either carboxylic acids or with thioacids wherein said ester groups are in trans position with respect to the nitrate group.

Patent application WO 2005/037842 describes isosorbide mononitrates wherein the free hydroxyl group has been replaced by a wide range of substituents.

A particular class of compounds disclosed in these publications is represented by the following formula (A)

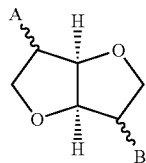

(A)

wherein one of A and B represents —ONO$_2$ and the other represents —S—CO—R, wherein R is a $C_{1-4}$ alkyl group, an aryl group or an aralkyl group, eventually substituted. According to these publications the disclosed dioxa-bicyclooctane compounds may be prepared by thioacetylation of a compound of formula (B):

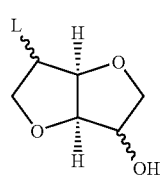

(B)

wherein L represents a leaving group, isolating the thioacetylated product by chromatography, carrying out a nitration reaction, and then purifying the compounds of interest by another chromatographic treatment.

This preparation method affords less than 20% overall yield and involves chromatographic treatments after the thioacetylation step as well as after the nitration reaction. In addition the nitration step involved the use of a mixture of nitric acid, acetic acid and acetic anhydride which is unsatisfactory from a safety point of view. The need of chromatographic treatment and the use of unsafe nitrating agents are extremely disadvantageous for industrial-scale synthetic preparations. Furthermore, both the low yield and the purification by chromatography are highly undesirable from an economic point of view.

SUMMARY OF THE INVENTION

In view of the above drawbacks, it is an object of the present invention to provide a new preparation method for dioxa-bicyclooctane nitrate compounds, which does not involve a chromatographic treatment and results in higher overall yields and makes use of a safe nitrating agent.

The present inventors have developed a novel stereospecific preparation method for dioxa-bicyclooctane nitrate compounds in which no chromatographic purification is required and products of high purity and in good yields are obtained.

It also an object of the present invention to produce novel intermediates for use in the new preparation method for dioxa-bicyclooctane nitrate compounds.

DETAILED DESCRIPTION OF THE INVENTION

In one aspect the present invention provides a method for the preparation of compounds according to formula (I):

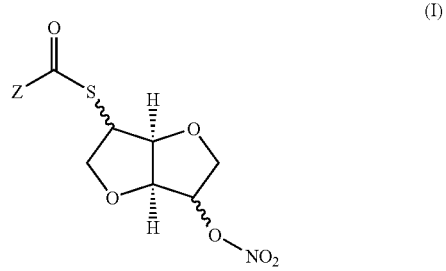

(I)

wherein z represents a $C_{1-6}$-alkyl, $C_{2-6}$-alkenyl, $C_{3-8}$-cycloalkyl, aryl, heteroaryl, aryl-$C_{1-6}$-alkyl, or heteroaryl-$C_{1-6}$-alkyl group, optionally substituted by one to three groups independently chosen from the group consisting of halogen, $C_{1-6}$-alkyl and $C_{1-6}$-alkylthio, comprising the following steps:

(a) reacting a compound of formula (II):

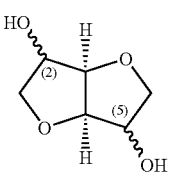

(II)

with a sulfonic derivative of formula (III)

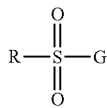
(III)

wherein the R is chosen from the groups $C_{1-3}$-alkyl, $C_{1-3}$-alkyl substituted with 1 to 3 halogen atoms, phenyl, $C_{1-3}$-alkyl-phenyl and $C_{1-3}$-alkyl-phenyl wherein the alkyl is substituted with 1 to 3 halogen atoms and G is a halogen atom or a group —O—SO$_2$—R wherein R is as hereinabove defined to yield a compound of formula (IV)

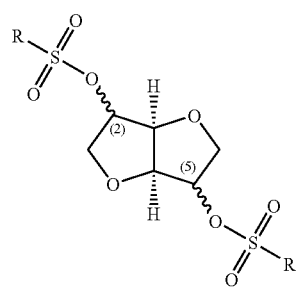
(IV)

whereby the configuration of carbons (2) and (5) remains substantially unchanged;

(b) treating compound (IV) with a thiocarboxylic acid of formula (V) or a salt thereof:

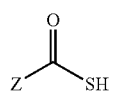
(V)

wherein Z is as defined above, to yield compound (VI)

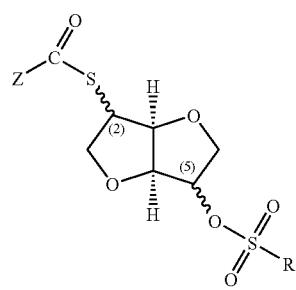
(VI)

wherein R has the meaning defined for formula (III) and whereby the configuration of carbon (2) is substantially inverted;

(c) treating compound (VI) with tetrabutylammonium nitrate to yield a compound of formula (I) whereby the configuration of carbon (5) is substantially inverted;

In another aspect the present inventions provides for new intermediates of formula (VI).

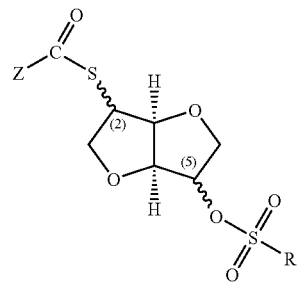
(VI)

wherein R is chosen from the groups $C_{1-3}$-alkyl, $C_{1-3}$-alkyl substituted with 1 to 3 halogen atoms, phenyl, $C_{1-3}$-alkyl-phenyl and $C_{1-3}$-alkyl-phenyl wherein the alkyl is substituted with 1 to 3 halogen atoms and Z represents a $C_{1-6}$-alkyl, $C_{2-6}$-alkenyl, $C_{3-8}$-cycloalkyl, aryl, heteroaryl, aryl $C_{1-6}$-alkyl, or heteroaryl-$C_{1-6}$-alkyl group, optionally substituted by one to three groups independently chosen from the group consisting of halogen, $C_{1-6}$-alkyl and $C_{1-6}$-alkylthio.

In yet another aspect the present invention provides for new intermediates of formula (IV)

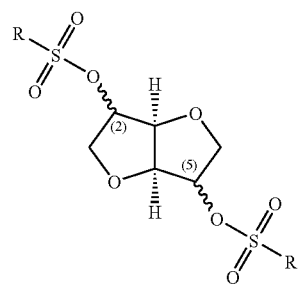
(IV)

wherein R represents a trifluoromethyl group.

The compounds of formula (II) comprise isosorbide, isomannide and isoidide which are commercially available.

The reactions of steps (b) and (c) appear to take place as a bimolecular nucleophilic substitution ($S_N2$) reaction since substantial inversion of the configuration in the carbon atom is observed.

As mentioned above, the process of the invention is stereospecific maintaining the relative configuration of carbons (2) and (5). Thus, when in the starting product of formula (II) the two hydroxyl groups are trans to each other, the resulting product of formula (I) has a thiocarboxylate Z—C(=O)—S— group which is trans to the nitrate group. When a starting product with cis configuration is used, in the resulting product the thiocarboxylate Z—C(=O)—S— group is cis to the nitrate group.

The subsequent nitration reaction simplifies the previously known method disclosed, for example in WO 00/20420, because the products obtained do not need to be purified by chromatography. This is highly advantageous not only under economic considerations but also in view of the easier handling of the synthesis. The nitration reaction is carried out using tetrabutylammonium nitrate as a safe nitrating agent.

Surprisingly, the method of the present invention provides higher yield and purity compared to those disclosed in the state of the art documents. The overall yield for the preparation of compounds of formula (I) from compounds of formula (II) is increased compared to the method disclosed in WO 00/20420 and often exceeds 40%. Also the purity of the compounds obtained by the method of the present invention makes unnecessary to undertake a step of purification by chromatography as it is disclosed in this document.

Furthermore, as has been outlined above, the relative stereochemistry at the C2 and C5 position is the same in the final product (I) and in the starting product (II).

The general terms used in this specification have the meaning indicated below:

The term "$C_{1-6}$-alkyl" refers to a straight or branched hydrocarbon chain radical having 1 to 6 carbon atoms and which is attached to the rest of the molecule by a single bond, e.g., methyl, ethyl, n-propyl, isopropyl, n-butyl, iso-butyl, sec-butyl, t-butyl, n-pentyl, n-hexyl, etc.

The term "$C_{1-3}$-alkyl" refers to a straight or branched hydrocarbon chain radical having 1 to 3 carbon atoms and which is attached to the rest of the molecule by a single bond, e.g., methyl, ethyl, n-propyl, isopropyl.

The term "$C_{2-6}$-alkenyl" refers to a straight or branched hydrocarbon chain radical, having 2 to 6 carbon atoms and at least one double bond of either E or Z stereochemistry where applicable, e.g., vinyl, allyl, 1-butenyl, 2-butenyl, and 2-methyl-2-propenyl.

The term "$C_{3-8}$cycloalkyl" refers to an alicyclic group having 3 to 8 carbon atoms, e.g., cyclopropyl, cyclobutyl, cyclopentyl and cyclohexyl.

Aryl refers to an aromatic hydrocarbon radical, preferably with 6 to 14 carbon atoms, e.g., phenyl, naphthyl, fluorenyl, or phenanthryl, whereby said radicals are unsubstituted or substituted by one or more substituents independently of one another, preferably up to three, primarily one or two substituents, especially those chosen from unsubstituted, mono- or di-substituted amino, halogen, unsubstituted or substituted alkyl, free, etherified or esterified hydroxy, nitro, cyano, free or esterified carboxy, alkanoyl, unsubstituted, N-mono- or N,N-di-substituted carbamoyl, amidino, guanidino, mercapto, phenylthio, phenylsulfinyl, phenylsulfonyl, ethenyl, phenyl, methylthio, acetyl, methylmercapto ($CH_3S$—), trifluoromethylmercapto ($CF_3S$—), trifluoromethylsulfonyl, and methylenedioxy bound to adjacent carbon atoms of the ring; aryl is for example phenyl which is unsubstituted or is substituted by one or two substituents, independently of one another, chosen from the group consisting of amino, acetylamino, fluorine, chlorine, bromine, methyl, ethyl, propyl, or t-butyl, trifluoromethyl, hydroxy, methoxy, ethoxy, benzyloxy, and cyano, or (as an alternative or in addition to the above group of substituents) n-decyloxy, carbamoyl, N-methyl- or N-tert-butylcarbamoyl, acetyl, phenyloxy, trifluoromethoxy or 1,1,2,2-tetrafluoroethoxy, ethoxycarbonyl, methyl mercapto, trifluoromethylmercapto, hydroxymethyl, 1-hydroxyethyl, methylsulfonyl, trifluoromethylsulfonyl, phenylsulfonyl, 2-methyl-pyrimidin-4-yl, oxazol-5-yl, 2-methyl-1,3-dioxolan-2-yl, pyrazol-3-yl, methyl-pyrazol-3-yl and methylenedioxy bound to two adjacent carbon atoms; especially preferred are one or two substituents chosen independently of one another from methyl, chlorine or bromine, and trifluoromethyl. Aryl in the form of phenyl which is substituted by methylene dioxy is preferably 3,4-methylene dioxyphenyl. Aryl is most preferably phenyl which is preferably unsubstituted or substituted by one or more substituents chosen independently of one another from the group consisting of methyl, ethyl, n-propyl, i-propyl, t-butyl, fluorine, chlorine, bromine, methoxy, trifluoromethyl; phenyl is most preferably unsubstituted or substituted by one or two substituents chosen independently of one another from the group consisting of methyl, ethyl, isopropyl or t-butyl, bromine, chlorine, fluorine, and trifluoromethyl.

Heteroaryl refers to an unsaturated heterocyclic radical and is mono-, bi- or tricyclic, preferably monocyclic, whereby, one or more, preferably one to four, especially one or two, most preferably one carbon atom(s) of a corresponding aryl radical are replaced by a hetero atom chosen from the group consisting of nitrogen, oxygen and sulfur, whereby the binding ring has preferably 4 to 12, especially 5 to 7 ring atoms; whereby heteroaryl said radical is unsubstituted or is substituted by one or more, especially 1 to 3, substituents chosen independently from the group consisting of the above-mentioned substituents of aryl; and it is in particular a heteroaryl radical chosen from the group consisting of imidazolyl, thienyl, furyl, pyranyl, thianthrenyl, isobenzofuranyl, benzofuranyl, chromenyl, 2H-pyrrolyl, pyrrolyl, imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indazolyl, triazolyl, tetrazolyl, purinyl, quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl, furazanyl, etc.

The term "aryl-$C_{1-6}$-alkyl" refers to an aryl group attached to a $C_{1-6}$-alkyl group, e.g., phenylmethyl, phenylethyl, phenylpropyl, phenylbutyl, phenylpentyl, phenylhexyl, naphthylmethyl, naphthylethyl, naphthylbutyl, fluorenylmethyl, fluorenylethyl, fluorenylbutyl, phenanthrylethyl and phenanthrylbutyl, which are unsubstituted or substituted as explained above for aryl. Preferably aryl-$C_{1-6}$-alkyl relates to phenylmethyl, phenylpropyl, phenylpentyl, and naphthylmethyl, whereof phenylpropyl is most preferred.

The term "heteroaryl-$C_{1-6}$-alkyl" refers to a heteroaryl group which is attached to a $C_{1-6}$-alkyl group, e.g., imidazolylmethyl, imidazolylethyl, imidazolylbutyl, thienylmethyl, thienylethyl, thienylbutyl, furylmethyl, furylethyl, furylbutyl, furylhexyl, pyranylethyl, pyranylbutyl, pyrrolylethyl, pyrrolylethyl, pyrrolylbutyl, pyrrolylhexyl, imidazolylethyl, imidazolylbutyl, pyridylethyl, pyridylbutyl, pyrazinylethyl, and pyrazinylbutyl, which are unsubstituted or substituted as explained above for heteroaryl. Preferably heteroaryl-$C_{1-6}$-alkyl relates to thienylmethyl, furylmethyl, pyranylmethyl, imidazolylmethyl, pyridylmethyl, and pyridylpropyl, whereof pyridylmethyl is most preferred.

The term "5-, 6- or 7-membered ring" refers to an alicyclic ring containing either no or at least one double bond, e.g., cyclopentane, cyclohexane, cyclopentene, cyclohexene, etc.

In an embodiment of the preparation method of the present invention, in formula (I) the thiocarboxylate Z—C(=O)—S— group is trans to the nitrate group.

In an embodiment of the preparation method of the present invention, in formula (I) the thiocarboxylate Z—C(=O)—S— group is cis to the nitrate group.

In another embodiment of the present invention the sulfonic derivative of formula (III) is a sulfonyl chloride or a sulfonyl anhydride.

In another embodiment of the present invention the sulfonic derivative of formula (III) is chosen from the group comprising trifluoro-methanesulfonic anhydride, 4-methylbenzesulfonic anhydride or methylsulfonic anhydride, preferably trifluoro-methanesulfonic anhydride.

In another embodiment of the present invention the reaction of compounds of formula (II) with a sulfonic derivative (III) to yield compounds of formula (IV) is carried out in an aprotic solvent able to solubilise both reactants are soluble in particular those in which the solubility of both starting products (II) and (III) is at least 1 g/l: Examples of suitable solvents are dichloromethane, toluene or xylene. The reaction of (II) and (III) takes places in the presence of an inorganic base such as $K_2CO_3$, NaOH or an organic base such as a secondary or tertiary amine. Preferably the amine is chosen from the group comprising diethylamine, triethylamine and pyridine, in particular pyridine. The reaction conveniently takes place at room temperature during 1 to 2 hours.

In still another embodiment of the present invention, residue Z both in compound (I) and (V) represents a $C_{1-6}$-alkyl, $C_{2-6}$-alkenyl, aryl, or heteroaryl group, which group may be unsubstituted or substituted. Preferably Z represents a $C_{1-6}$-alkyl group, more preferably methyl, ethyl, n-propyl, or n-butyl, and most preferably methyl In another embodiment the thiocarboxylation reaction can be carried out with a salt of the thiocarboxylic acid of formula (V). Examples of suitable salts are those in which the cation is chosen from an alkali metal or an earth alkali metal. Specially preferred alkali metals or earth alkali metals are sodium, potassium, cesium, magnesium and calcium, potassium being particularly preferred.

In another embodiment of the present invention the reaction of compounds (IV) with the thiocarboxylic acid of formula (V) or a salt thereof to yield compound (VI) is carried out by dissolving or suspending compound (IV) in an aprotic solvent such as toluene or xylene and reacting this solution with an aqueous solution of the thiocarboxylic acid of formula (V) in the presence of a phase transfer catalyst. The choice of the phase transfer catalyst does not seem critical and compounds such as hexadecyltributylphosphonium bromide, tricaprylmethylammonium chloride, methyltrioctylammonium chloride and tributylammonium chloride may be used. The reaction conveniently takes place at a temperature of 50-80° C., preferably 60-70° C. during 2 to 6 hours, preferably 3 to 4 hours.

In another embodiment of the present invention the nitration of the compounds of formula (VI) to yield the compounds of formula (I) is carried out by adding tetrabutylammonium nitrate to a solution of compound (IV) in an aprotic solvent such as toluene or xylene and heating the mixture at 60-90° C., preferably 70-80° C. during 2 to 8 hours, preferably 4 to 6 hours. It is possible to use the solution of compound (VI) from the previous reaction step without isolation of the compound.

The working examples included in the present specification describe in detail suitable processes to obtain several of the compounds according to general formula (I). In the light of these examples, it is within the general knowledge of the expert in the field to obtain the compounds not explicitly exemplified by suitable modifications of the working examples. It is also obvious for the expert in the field that these examples are only illustrative and should not be taken as a limitation of the scope of the invention.

EXAMPLES

The compounds obtained in the examples described below are identified by their proton ($^1$H-NMR) and carbon-13 ($^{13}$C-NMR) nuclear magnetic resonance spectroscopic data.

The Nuclear Magnetic Resonance spectra were recorded using a Varian Gemini-2000 apparatus.

The operating frequency and the solvent used to record the spectra are indicated in the $^1$H-NMR spectra. The signal's positions are indicated in δ (ppm) and the signal from the solvent's protons is taken as a reference. The reference values were 7.24 ppm for deuterated chloroform and 2.49 ppm for hexadeuterated dimethyl sulfoxide. The signal obtained for tetramethylsilane's (TMS) protons is occasionally taken as an internal standard, with a reference value of 0 ppm. Within brackets are indicated the number of protons corresponding to each signal measured by electronic integration and the type of signal using the following abbreviations: s (singlet), d (doublet), t (triplet), q (quadruplet), dd (doublet of doublets), ddd (doublet of doublet of doublets), bs (broad signal), m (multiplet), cs (complex signal), s.a. $D_2O$ (simplifies upon deuteration), d.a. $D_2O$ (disappears upon deuteration).

The $^{13}$C-NMR spectra indicate the working frequency and the solvent used to run the spectrum. The position of the signals is indicated in δ (ppm), using the central signal of the solvent as reference. The reference values are 77.00 ppm for deuterated chloroform and 39.50 ppm for hexadeuterated dimethyl sulfoxide.

In the experimental part, the following abbreviations are used:

Tf Triflate (trifluoromethanelsulfonate)

Example 1

Synthesis of 2-acetylthio-isosorbide 5-mononitrate

Step 1: Preparation of Isosorbide Ditriflate

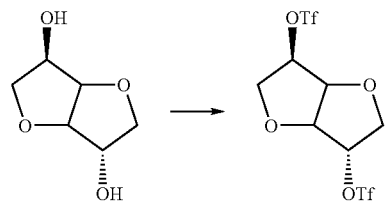

Isosorbide (300 g), dichloromethane (7.5 L, 9.938 Kg) and pyridine (0.586 Kg) are charged to a 20 L flange flask. The resultant solution is cooled (3° C.) with stirring. Trifluoromethanesulfonic anhydride (0.749 L, 1.257 Kg) is added to the solution via dropping funnel.

The reaction is stirred out to room temperature for 1-2 hours and the reaction is quenched by the cautious addition of water (1.5 Kg).

The organic layer is removed and the aqueous layer is re-extracted with dichloromethane (0.750 L).

All organic layers are washed with 5M HCl acid solution and with water until neutral pH.

The organic layers are charged to 7.5 L of heptane, after that the dichloromethane was removed from the product mixture by distillation using partial vacuum such that vessel temperature does not exceed 50° C.

The resultant precipitate is cooled to 3° C. stirred for at least 30 min and then filtered. The filter cake is washed with cold heptane and dried at 30-35° C. under house vacuum to yield a white crystalline solid. Yield: 0.822 Kg (97.6%)

$^1$H-NMR (200 MHz, CDCl$_3$)

5.42-5.35 (1H, sc, C<u>H</u>—O—SO$_2$CF$_3$); 5.34-5.24 (1H, sc, C<u>H</u>—O—SO$_2$CF$_3$); 5.10-4.99 (1H, sc, C<u>H</u>—O—C); 4.71

(1H, d, J=5.2, CH—O—C); 4.42-4.08 (3H, sc, H—CH—CHOSO$_2$CF$_3$, CH$_2$—CHOSO$_2$CF$_3$); 3.94 (1H, dd, J=4.8, J=11.8, H—CH—CHOSO$_2$CF$_3$)

$^{13}$C-NMR (50 MHz, CDCl$_3$)

118.44 (q, J=317.5, CF3-SO2-O—); 118.37 (q, J=317.5, CF3-SO2—O—); 88.29 (CH—O—C); 85.91 (CH—O—C); 84.93 (CH—O—SO$_2$CF$_3$); 81.00 (CH—O—SO$_2$CF$_3$); 73.15 (CH$_2$); 71.35 (CH$_2$)

Step 2: Preparation of Isoidide 2-Thioacetate-5 Triflate

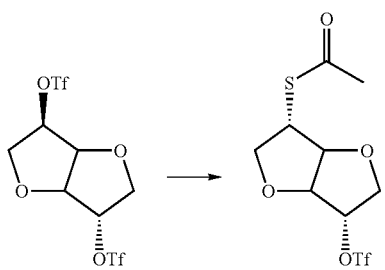

Isosorbide ditriflate (0.800 Kg) and toluene (4.00 L, 3.47 Kg) are charged to a 20 L flange flask. The suspension is heated with stirring to 35-45° C.

Potassium thioacetate (0.345 Kg) and water (2.00 L) are charged to a suitable sized conical flask. The contents of the flask are stirred until a solution is obtained.

To the potassium thioacetate solution is charged a solution of tetrabutylammonium chloride hydrate (0.044 Kg) in water (0.45 L). The resultant mixture is stirred at 15-25° C. for 0.25-0.5 h and then filtered.

The filtered potassium thioacetate/tetrabutylammonium chloride solution is charged to the toluene suspension. The resultant bi-phasic mixture is heated to 60-70° C. for 3-4 h.

The mixture is allowed to separate and the lower aqueous layer is run off and retained. The lower aqueous layer is re-extracted with toluene (1.0 L). The organic extracts are washed with water.

The solution can be used without isolation in next step. A sample of this solution is dried and the final product was characterized by RMN.

1H-NMR (200 MHz, CDCl$_3$)

5.36-5.26 (1H, sc, CH—O—SO$_2$CF$_3$); 4.80-4.70 (2H, sc, CH—CHSCOMe, CH—CHOSO$_2$CF$_3$); 4.23-3.96 (4H, sc, H—CH—CHOSO$_2$CF$_3$, CH$_2$CHS, CH—S); 3.84 (1H, dd, J=9.6, J=2.6, H—CH—CHOSO$_2$CF$_3$); 2.38 (3H, S, CH$_3$)

$^{13}$C-NMR (50 MHz, CDCl$_3$)

193.71 (C=O); 118.36 (q, J=317.9, CF3-SO2-O—); 88.94 (CH—CHSCOMe); 87.32 (CH—CHOSO$_2$CF$_3$); 85.15 (CH—O—SO$_2$C$_3$); 72.94 (CH$_2$CHS); 72.20 (CH$_2$—CHOSO$_2$CF$_3$); 47.81 (CH—S); 30.54 (CH$_3$)

Step 3: Preparation of Isosorbide 2-Thioacetate-5-Nitrate

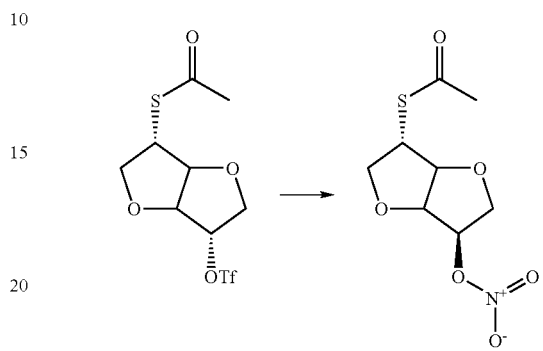

The solution obtained in step 2 and tetrabuylammonium nitrate (0.891 Kg) are charged to a 20 L flange flask. The resultant mixture is heated to 70-80° C. for 4-6 h. The mixture is allowed to separate and the lower dark-coloured ammonium triflate is run off and re-extracted with toluene (3×2.0 L). The combined extracts are washed with water (3×2.25 L).

The organic solution is concentrated by distillation 9.85 L of toluene under reduced pressure (temp<50° C.). To the concentrate solution is charged activated carbon (0.03 Kg) and stirred at 45-55° C. for 1-1.5 h.

The solution was filtered and the carbon residue is washed with toluene. The carbon-treated toluene solution is then added slowly to stirred heptane (7.5 L). The resultant product suspension is cooled, stirred and filtered.

The product is washed with cold heptanes and dried under vacuum at 30-35° C. (0.232 Kg; 47.7%)

Crude isosorbide 2-thioacetate-5-nitrate and 2-Propanol were charged to a 2 L flange flask. The resultant suspension is heated with stirring to 45-55° C. until a clear solution was obtained.

The solution was allowed to cool to room temperature with stirring (1.5 h) and cooled to 0-5° C. and maintained at this temperature for at least 1.0 h.

The product was filtered, washed with cold 2-Propanol and dried under vacuum (30-35° C.)

The product obtained is a white crystalline powder (0.212 Kg; 94.9%)

$^1$H-NMR (200 MHz, CDCl$_3$)

5.33 (1H, ddd, J=5.6, J=2.9, J=5.6, H—CONO$_2$); 4.92-4.86 (1H, sc, H—C—CHONO$_2$); 4.45 (1H, d, J=4.6, H—C—CHS); 4.21 (1H, dd, J=4.6, J=9.6, H—CH—CHS); 4.11-4.02 (2H, sc, H—CH—CHONO$_2$, H—CS); 3.96-3.84 (2H, sc, H—CH—CHS, H—CH—CHONO$_2$); 2.36 (3H, s, CH$_3$)

$^{13}$C-NMR (50 MHz, CDCl$_3$)

194.15 (C=O); 88.52 (CH—CHSCOMe); 81.47 (CH—CHONO$_2$); 81.24 (CHONO$_2$); 73.54 (CH$_2$CHS); 69.31 (CH$_2$CONO$_2$); 48.05 (CH—S); 30.66 (CH$_3$)

The invention claimed is:
1. A method for the preparation of a compound of formula (I):

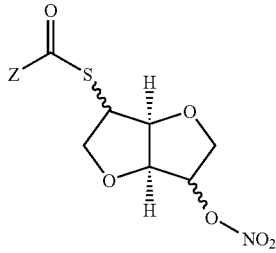

wherein Z represents a $C_{1-6}$-alkyl, $C_{2-6}$-alkenyl, $C_{3-8}$-cycloalkyl, aryl, heteroaryl, aryl $C_{1-6}$-alkyl, or heteroaryl-$C_{1-6}$-alkyl group, optionally substituted by one to three groups independently chosen from the group consisting of halogen, $C_{1-6}$-alkyl and $C_{1-6}$-alkylthio,
comprising the following steps:
(a) reacting a compound of formula (II):

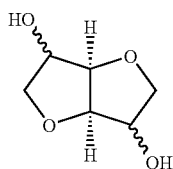

with a sulfonic derivative of formula (III)

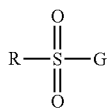

wherein R is chosen from the group consisting of $C_{1-3}$-alkyl, $C_{1-3}$-alkyl substituted with 1 to 3 halogen atoms, phenyl, $C_{1-3}$-alkyl-phenyl and $C_{1-3}$-alkyl-phenyl; wherein the alkyl is substituted with 1 to 3 halogen atoms and G is a halogen atom or —O—$SO_2$—R; wherein R is as hereinabove defined, to yield a compound of formula (IV)

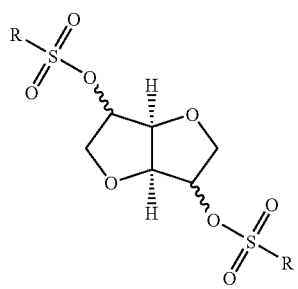

wherein R has the meaning defined for formula (III);
(b) treating compound (IV) with a thiocarboxylic acid of formula (V) or a salt thereof:

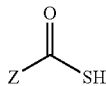

wherein Z is as defined for formula (I), to yield compound (VI);

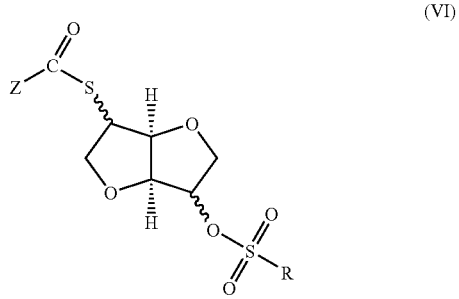

wherein Z is as defined for formula (I) and R is as defined for formula (III); and
(c) treating compound (VI) with tetrabutylammonium nitrate to yield a compound of formula (I).
2. The method according to claim 1, wherein in the compound of formula (I), the thiocarboxylate Z—C(=O)—S— group is trans to the nitrate group.
3. The method according to claim 1, wherein Z represents a $C_{1-6}$-alkyl, $C_{2-6}$-alkenyl, aryl, or heteroaryl group.
4. The method according to claim 3, wherein Z is chosen from the group consisting of methyl, ethyl, n-propyl, or n-butyl.
5. The method according to claim 4, wherein Z represents a methyl group.
6. The method according to claim 1 wherein a sodium, potassium, cesium, magnesium or calcium salt of the thiocarboxylic acid of formula (V) is used.
7. The method according to claim 6 wherein a potassium salt of the thiocarboxylic acid of formula (V) is used.
8. The method according to claim 1 wherein the sulfonic derivative of formula (III) is chosen from a sulfonyl chloride or a sulfonyl anhydride.
9. The method according to claim 8 wherein the sulfonic derivative of formula (III) is from the group consisting of trifluoro-methanesulfonic anhydride, 4-methylbenzesulfonic anhydride and ethylsulfonic anhydride.
10. The method according to claim 9 wherein the sulfonic anhydride is trifluoro-methanesulfonic anhydride.
11. The method according to claim 1 wherein step b) is carried out by dissolving compound (IV) in an aprotic solvent and reacting this solution with an aqueous solution comprising a thiocarboxylic acid of formula (V) or a salt thereof in the presence of a phase transfer catalyst.
12. The process according to claim 1 wherein step c) is carried out using the reaction mixture from claim b) without isolating the compound of formula (VI).
13. The method according to claim 1 wherein step c) is carried out using tetrabutylammonium nitrate as a nitrating agent.
14. The method according to claim 13 wherein step b) is carried out by adding tetrabutylammonium nitrate to a solution of compound (IV) in an aprotic solvent.

15. The method according to claim 14 wherein the reaction of step c) is carried out by heating the mixture at a temperature from 60 to 90° C. during a period of 2 to 8 hours.

16. The method according to claim 1 wherein step c) is carried out using the reaction mixture from claim b) without isolating the compound of formula (VI).

17. A compound of formula (VI)

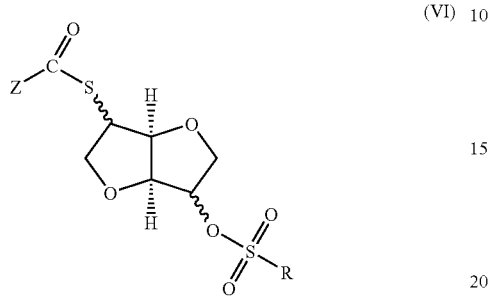

(VI)

wherein R is selected from the group consisting of $C_{1-3}$-alkyl, $C_{1-3}$-alkyl substituted with 1 to 3 halogen atoms, phenyl, $C_{1-3}$-alkyl-phenyl and $C_{1-3}$-alkyl-phenyl;

wherein the alkyl is substituted with 1 to 3 halogen atoms and Z represents a $C_{1-6}$-alkyl, $C_{2-6}$-alkenyl, $C_{3-8}$-cycloalkyl, aryl, heteroaryl, aryl $C_{1-6}$-alkyl, or heteroaryl-$C_{1-6}$-alkyl group, optionally substituted by one to three groups independently chosen from the group consisting of halogen, $C_{1-6}$-alkyl and $C_{1-6}$-alkylthio.

18. A compound of formula (IV)

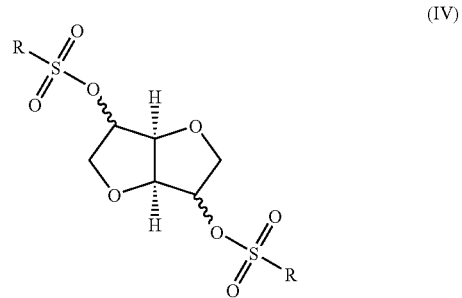

(IV)

wherein R represents a trifluoromethyl group.

* * * * *